United States Patent
Goldfarb et al.

(10) Patent No.: US 11,207,202 B2
(45) Date of Patent: *Dec. 28, 2021

(54) UPPER EXTREMITY ASSISTANCE DEVICE

(71) Applicant: Vanderbilt University, Nashville, TN (US)

(72) Inventors: Michael Goldfarb, Franklin, TN (US); Benjamin Gasser, Nashville, TN (US); Judith Lefkowitz, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 160 days.

This patent is subject to a terminal disclaimer.

(21) Appl. No.: 16/804,216

(22) Filed: Feb. 28, 2020

(65) Prior Publication Data

US 2020/0197208 A1 Jun. 25, 2020

Related U.S. Application Data

(63) Continuation of application No. 14/929,789, filed on Nov. 2, 2015, now Pat. No. 10,610,399, which is a continuation of application No. PCT/US2014/036598, filed on May 2, 2014.

(60) Provisional application No. 61/818,604, filed on May 2, 2013.

(51) Int. Cl.
*A61F 5/01* (2006.01)
*A61H 1/02* (2006.01)

(52) U.S. Cl.
CPC ...... *A61F 5/013* (2013.01); *A61F 2005/0137* (2013.01); *A61F 2005/0158* (2013.01); *A61F 2005/0165* (2013.01); *A61H 1/0277* (2013.01); *A61H 1/0285* (2013.01); *A61H 1/0288* (2013.01)

(58) Field of Classification Search
CPC .. A61H 1/0274; A61H 1/0277; A61H 1/0285; A61H 1/0288; A61F 5/013; A61F 2005/0137; A61F 2005/0158; A61F 2005/0165
See application file for complete search history.

(56) References Cited

U.S. PATENT DOCUMENTS

| | | |
|---|---|---|
| 3,698,389 A | 10/1972 | Guedel |
| 5,848,979 A | 12/1998 | Bonutti |
| 5,891,061 A | 4/1999 | Kaiser |
| 7,473,234 B1 | 1/2009 | Wellner |
| 8,100,844 B2 | 1/2012 | DeHarde |

(Continued)

FOREIGN PATENT DOCUMENTS

WO    WO 0158392 A1    8/2001

OTHER PUBLICATIONS

International Search Report for International Application No. PCT/US2014/036598, dated Sep. 3, 2014 (2 pages).

*Primary Examiner* — Keri J Nelson
(74) *Attorney, Agent, or Firm* — Nixon Peabody LLP

(57) ABSTRACT

An orthotic device includes an upper arm section for receiving an upper portion of an arm of a subject, a forearm section for receiving a forearm section of the arm, and at least one elbow joint rotatably coupling the upper arm section and the forearm section. In the orthotic device, the forearm section includes a release control operatively coupled to the at least one elbow joint, where the release control is configured to transition the at least one elbow joint from a restricted motion state to a free motion state when the release control is activated.

15 Claims, 3 Drawing Sheets

(56) References Cited

U.S. PATENT DOCUMENTS

| | | |
|---|---|---|
| 8,273,042 B2 | 9/2012 | Lidolt |
| 10,610,399 B2 * | 4/2020 | Goldfarb ................. A61F 5/013 |
| 2005/0165337 A1 | 7/2005 | Weiss |
| 2013/0072829 A1 | 3/2013 | Fausti |

* cited by examiner

UPPER EXTREMITY ASSISTANCE DEVICE

CROSS-REFERENCE TO RELATED APPLICATIONS

This application is a continuation of U.S. patent application Ser. No. 14/929,789 filed on Nov. 2, 2015, which is a by-pass continuation of International Application No. PCT/US2014/036598 filed on May 2, 2014, which claims priority to and the benefit of U.S. Provisional Application No. 61/818,604, filed May 2, 2013 and entitled "Upper Extremity Assistance Device", the contents of which are herein incorporated by reference in their entirety.

FIELD OF THE INVENTION

The present invention relates to orthotic devices for upper extremities, and more specifically to orthotic devices for managing non-functional upper extremities.

BACKGROUND

A large number of persons commonly suffer from hemiparesis or hemiplegia. Persons with hemiparesis suffer from weakness on one side of the body. That is, the patient can move an arm, leg, and/or trunk associated with an impaired side of their body, but with reduced muscular strength. Persons with hemiplegia are afflicted with paralysis of the arm, leg, and/or trunk on the same side of the body. Hemiplegia and hemiparesis may be congenital, or they might be acquired conditions resulting from an illness, an injury, or a stroke.

Whether a person is suffering from hemiparesis or hemiplegia, the end result is extreme difficulty performing everyday tasks. In particular, many activities of daily living entail bimanual tasks, which either require or are greatly facilitated by the use of two hands. In many bimanual tasks, one arm and hand are used essentially to provide support or resistance, while the other arm and hand are used to provide power or movement. Examples include twisting a lid off of a jar, slicing a loaf of broad, turning the page of a book, taking currency out of a wallet, etc. Still other tasks use one or both arms to hold an object, but do not otherwise require motive power. Examples include holding a bag or briefcase (single-arm holding tasks), or holding a laundry basket (bimanual holding task).

SUMMARY

Embodiments of the invention concern orthotic devices for managing non-functional or diminished function upper extremities. The various embodiments described herein enable a person with upper extremity hemiplegia or hemiparesis to conduct certain manual or bimanual tasks that use the paretic limb for holding, and rely on the non-paretic limb to configure the paretic limb, and to provide any power or movement required to perform the task or activity. Relatively simple tasks, such as twisting a jar open, grasping objects, or using eating utensils, can be extremely difficult for a person with hemiparesis or hemiplegia affecting an upper extremity, as they may no longer possess the requisite strength or capabilities in their affected upper extremity to perform the activity.

In a first embodiment, an orthotic device for the upper limb compromises at least an elbow joint, where the elbow joint is configured to be in a normally-locked state, and is further configured to be in a free state by a release mechanism, wherein the release mechanism is actuated by a lever, button, or functionally similar element, located on the distal forearm.

In the device of the first embodiment, the lever or button can be actuated by applying a constrictive force around the distal forearm, such as by grasping and squeezing the distal forearm. In some configurations, maintaining the orthotic device in the free state requires a continuous grasping and squeezing of the lever or button on the distal forearm. In other configurations, successive squeezing toggles the elbow joint to be in either the free state or the locked state.

In operation, the lever or button can pull a cable, which releases a clutch mechanism within the elbow joint of the orthotic device. The clutch mechanism can be one of a friction clutch, a dog clutch, a wrapped spring clutch, or a belt clutch type. In some configurations, the release mechanism can be electrically actuated where an electrical switch controls an electrically-actuated clutch. The electrically-actuated clutch can be of the electromagnetic, electrorheological, magnetorheological, or magnetic particle types.

In the device, a passively repositionable wrist joint can be provided.

In a second embodiment, an orthotic device for the upper limb compromising at least an elbow joint and a wrist joint is provided, where the elbow and wrist joints of the orthotic device are simultaneously configured via a common mechanism to be in either a locked state, and where the elbow and wrist joints are locked, or in a free state in which the elbow and wrist joints are free to move. In the device, the wrist joint includes at least a wrist rotation degree of freedom. In some configurations, the wrist rotation joint can be situated on the proximal portion of the forearm.

In the device of the second embodiment, the joints can be in a normally-locked state with a common release mechanism that configures both joints to be in a free state. This release mechanism can be actuated by a lever, button, or functionally similar element, located on the distal forearm. In some configurations, the lever or button is actuated by applying a constrictive force around the distal forearm, such as by grasping and squeezing the distal forearm. Further, maintaining the orthotic device in the free state can require a continuous grasping and squeezing of the lever or button on the distal forearm.

In operation, the lever or button pulls a cable, which simultaneously releases respective clutch mechanisms within the wrist and elbow joints of the orthotic device. In some configurations, the device is configured in the free state only when a constrictive force is applied around the distal forearm. In other configurations, successive squeezing toggles the joints of the orthotic device to be in either the free state or the locked state.

In some configurations, multiple cables emanate from the single release lever, where each cable releases a clutch corresponding to a different joint. In other configurations, a single cable can emanate from the single release lever, wherein the single cable releases multiple clutches, each corresponding to a respective joint.

The clutch mechanisms can be of the friction clutch, dog clutch, wrapped spring clutch, or belt clutch type. In some configurations, the common release mechanism can be electrically actuated. Further, an electrical switch can be provided that controls a separate electrically-actuated clutch for each degree of freedom. Electrically-actuated clutches can be of the electromagnetic, electrorheological, magnetorheological, or magnetic particle types. In some configurations, a portion of the joints are configured to be in the free state via mechanical means and a portion of the joints are configured to be in the free state via electrical means.

In various embodiments, the orthotic device can further include a hand portion, where the joints of the hand portion provide assistance to at least a portion of the hand. Such a hand portion can incorporate elastic elements to assist with at least opening or closing of the digits of the hand. Further, at least one powered actuator can be employed to actively assist with at least the opening or closing of the hand. In some configurations, the hand portion can be configured to provide passive support of at least one digit of the hand. Further, a thumb portion of the hand portion can provide passive support of the thumb.

In some configurations, a button or switch can be situated on the hand portion of the device, where depressing the button or moving the switch moves the hand portion into an open and/or closed configuration. The button or switch can be situated on the thumb portion of the hand portion.

In some configurations, the actuator toggles the hand portion between the open and closed configurations when a transient movement or change in force at the at least one joint of the hand is detected. In such configurations, the movement or change of force detected is in the direction of opening the hand. Further, the actuator can toggle the hand portion from the open to the closed configuration when a transient movement or change in force at the at least one joint of the hand is detected in the direction of opening the hand. For example, the actuator can toggle the hand portion from the closed to the open configuration when a transient movement or change in force at the at least one joint of the hand is detected in the direction of closing the hand.

In some configurations, at least a portion of the hand portion can be situated on the posterior aspect of at least a portion of the digits of the hand, and where movement of the digits is accommodated by a remote center linkage, or a linkage with a joint center nominally aligned with the rotational axes of at least a portion of the hand digits.

In the various embodiments, the orthotic device can also be mated to a shoulder assistance portion. The shoulder assistance portion can be configured to support the orthotic device of the various embodiments. In some configurations, the shoulder assistance portion can also be configured to operate cooperatively or independently of orthotic device to allow a user to reposition an arm with respect to the shoulder joint.

DETAILED DESCRIPTION

Figure 1:
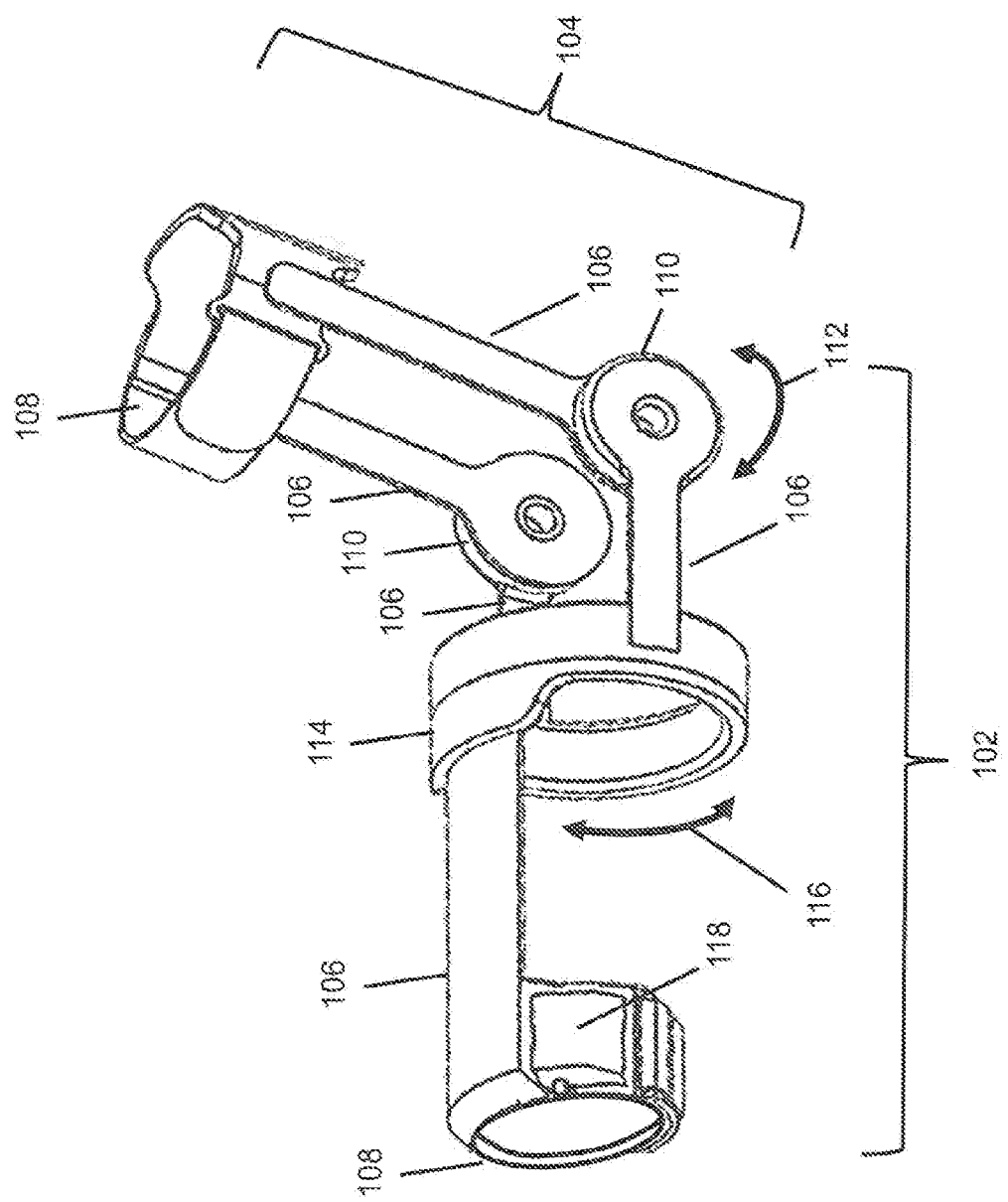
FIG. 1 shows an exemplary orthotic device in accordance with the present technology.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

To address the issues faced by persons with people with upper extremity neuromuscular deficits, due to hemiplegia, hemiparesis, or other conditions, the present technology provides upper extremity assistance devices configured to allow such persons greater mobility and use of their non-functional or paretic arm. In particular, an upper extremity assistance device in accordance with the present technology can be implemented as an orthotic device intended for people with one essentially functional arm (i.e., the non-paretic arm), and one essentially paretic arm, such as people with dense upper extremity hemiplegia, or with people with other neuromuscular impairments that present similarly (e.g., incomplete spinal cord injury, traumatic brain injury, or multiple sclerosis).

In accordance with the present technology, the orthotic device is worn on the paretic arm and includes in one embodiment an elbow joint and a wrist rotation joint. In the orthotic device, both of these joints are normally locked. Therefore, the paretic arm is maintained in a posture determined by the current configuration of the orthotic device. The person repositions the paretic arm as follows. First, a person can use their non-paretic arm to grasp a portion of the orthotic device near the distal forearm in a manner that activates a release mechanism. This mechanism can contemporaneously release both the elbow and wrist joints of the orthotic device into a freely moveable state. Second, while maintaining their grasp (and thus continuing to activate the release mechanism), the person can freely reposition the elbow and wrist joints for paretic arm. Therefore, the act of grasping the paretic arm has two purposes: it releases the normally-locked joints of the orthotic device and enables manipulation of the paretic arm, such that the paretic arm can be posed in a desired posture. After moving the paretic arm to a desired position or posture, the person can release their grasp around the distal forearm of the orthotic device, which deactivates the release mechanism. This causes both the elbow and wrist joints to contemporaneously return a locked state. In some embodiments, the location of the release mechanism is selected to substantially coincide with a likely location a person would grasp the paretic arm, such as around the distal forearm portion (i.e., near the anatomical wrist of the paretic arm). However, the present technology is not limited in this regard and other locations can be utilized for the release mechanism.

In some embodiments, the orthotic device can include a hand portion, which incorporates movement assistance for digits of a hand of the paretic arm. This movement assistance can be utilized to configure the hand of the paretic arm to grasp or release an object or to place the hand of the paretic arm in a particular posture. Additionally, the movement assistance can be configured to alternate the hand of the paretic arm between different postures. For example, the movement assistance for the hand portion can be configured to alternate the hand of the paretic arm between grasp and release postures. In some configurations, the hand portion can incorporate powered actuation to reconfigure the hand of the paretic arm between different postures.

The intent of the orthotic device of the present technology is to enable static posturing of the paretic arm and use of the paretic hand for grasping or holding objects. As noted above, a person can utilize their non-paretic arm to move the orthotic device, and thus the paretic arm, into various poses or postures and adjust the hand portion of the orthotic device, and thus the hand of the paretic arm, to effect grasp and release of an object. Accordingly, the person can use the paretic limb within the orthotic device to hold objects, or to perform certain bimanual tasks. For example, in order to twist a lid off of a jar (which is generally a bimanual task), the user would use their non-paretic arm to configure the paretic arm (and orthotic device) to grasp the jar, and would further position the joints of the arm such that the jar is held in front of the user (as opposed to by his or her side). Once held securely in the paretic arm with the aid of the orthotic device, the user can use their non-paretic hand and arm to twist the lid off the jar. In another example, holding a two-handed basket, the user would use their non-paretic arm to reposition the orthotic device, and thus the paretic arm and hand, to grasp one handle of the basket and use the non-paretic arm to grasp the other handle. In still another example, slicing a loaf of bread, the user can use their non-paretic arm to position the orthotic device, and thus paretic arm and hand, over the loaf of bread (e.g., on a countertop) to hold the loaf in place. Thereafter, the non-paretic arm can be used to slice the bread held in place by the paretic arm and hand.

Although the orthotic device of the present technology has been described with respect to repositioning of the elbow and wrist joints of the paretic arm, the present technology is not limited in this regard. In some configurations, a lockable joint can also be provided at the shoulder joint, where the shoulder joint can also be controlled by the orthotic device. However, the shoulder joint need not be explicitly locked in some instances, since in the absence of control of the shoulder, the arm and shoulder position will be governed primarily by gravitational forces and passive tissue characteristics in the shoulder joint. Thus, the position of the shoulder joint can be relatively stable, even in the absence of a locked joint.

Now turning to FIG. 1, there is shown an orthotic device 100 according to one embodiment of the present technology. The orthotic device 100 includes a forearm portion 102 and an upper arm portion 104, structural elements 106, and securing elements 108 in the forearm portion 102 and the upper arm portion 104, which attach the orthotic device 100 to the upper arm and forearm portions of the paretic arm. In FIG. 1, the securing elements 108 are arranged to attach the orthotic device 100 around the wrist of the paretic arm and around the biceps of the paretic arm. The orthotic device 100 also includes at least an elbow joint 110 that is normally locked to prevent motion 112 resulting in flexion or extension of the elbow of the paretic arm. The orthotic device 100 further includes a wrist joint 114. As shown in FIG. 1, the wrist joint can be situated at the proximal forearm, near the elbow joint 110. In general, the length of the structural elements 106 can be configured to be adjustable to allow a fit of the orthotic device to different users with difference arm lengths.

Although FIG. 1 is described as including a normally-locked joint associated with wrist pronation/supination, also referred to here as wrist rotation, the present technology is not limited in this regard. In other embodiments, the orthotic device 100 can include multiple normally-locked wrist degrees of freedom (e.g., wrist flexion/extension, ulnar/radial deviation, and pronation/supination).

In addition to the foregoing components, the orthotic device 100 also includes a release lever, button, or control 118. In the orthotic device, the release control 118 is positioned with the securing element 108 in the forearm portion 102. The release control 118 and the orthotic device are configured so that the elbow joint 110 and the wrist joint 104 are contemporaneously unlocked by grasping and squeezing the portion of the securing element 108 including the release control 118, near the anatomical wrist joint of the paretic limb. Thus, a user can reposition the paretic arm using their non-paretic arm.

In some embodiments, the release control 118 can be configured to pull at least one cable (not shown), which is routed along or within structural elements 106 and which releases a mechanical clutch mechanism (not shown) in joints 110 and 114 and enables free motion of these normally-locked joints. In another embodiment, the release control 118 can be an electrical switch wired (wires not shown) with one or more electrically-actuated clutches (not shown) in the joints 110 and 114, to simultaneously release the normally-locked joints. In another embodiment, a combination of mechanical and electrical release mechanisms are used. Regardless of the mechanism, the user can reposition the paretic arm into a desired pose. Once the release control 118 is released by user, the clutch mechanisms in joints 110 and 114 are re-engaged and the paretic arm is locked into the new pose.

As noted above, the mechanism by which the elbow joint 110 is unlocked can be mechanical or electrical. In embodiments with mechanical operation, activating the release control 118 situated at the distal forearm pulls a cable, which releases a clutch at the elbow joint 110 and the wrist rotation joint 114 of the orthotic device 100. The release control 118 can pull on multiple cables, which can release multiple clutch mechanisms situated in parallel, or can pull on a single cable, which releases multiple clutch mechanisms in series (i.e., daisy-chained together). Several clutch types will provide effective normally-locked joints that can be released via cable excursion, including friction clutch, dog clutch, wrapped spring clutch, and belt clutch variants. In embodiments with electrical operation, depressing the release control situated on the orthotic device at the distal forearm releases an electrically-actuated clutch, which releases the elbow joint 110 of the orthotic device 100. Several clutch types will provide effective normally-locked joints that can be released via electrical actuation, including electromagnetic, electrorheological, magnetorheological, and magnetic particle clutch types.

In some embodiments, the operation of the wrist rotation joint 114 and the elbow joint 100 can be separate. In some configurations, a different release control can be provided for each joint. In other configurations, the wrist rotation joint 114 can be passively repositionable, i.e., not directly coupled to the locking and unlocking of the elbow joint and rotatable with the application of sufficient force using the paretic arm.

In still other embodiments, the degree to which a joint is locked can vary. For example, the user may have diminished strength in the paretic arm and can utilize the orthotic device to stabilize this arm. However, for certain tasks, the user may not wish to have his elbow and wrist joints completely locked in place. Accordingly, in some configurations, the clutch/brake mechanism for joints 110 and 114 can be configured to allow some play. Further, in other configurations, the clutch/brake mechanism for joints 110 and 114 can be configured to allow motion when sufficient strength is applied by the user. For such alternative embodiments, the orthotic device 100 can be configured to allow such play as a default or can provide one or more additional controls (not shown) on orthotic device 100 to allow the user to adjust the amount of play as needed.

Figure 2:
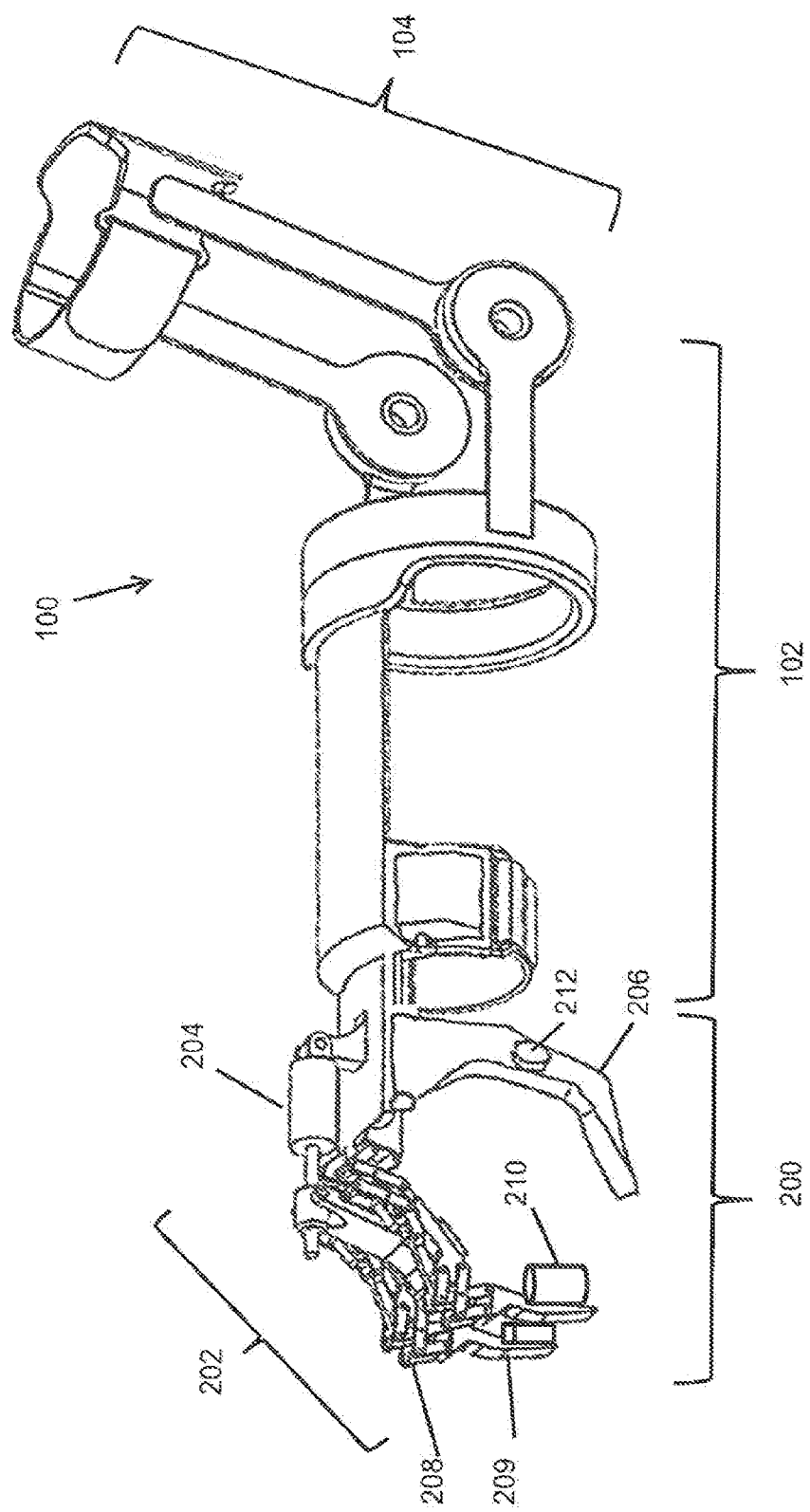
FIG. 2 the exemplary orthotic device of FIG. 1, outfitted with a hand portion in accordance with the present technology.

In some configurations, the orthotic device 100 can include a hand portion 200 attached to a distal end of forearm portion 102. This is illustrated in FIG. 2. The hand portion 200 can include first portions that actively assist with the opening and closing of the digits of the paretic arm and which can be combined with second portions that provide passive support. The first portions that assist with movement can include an actuator to provide active (or powered) movement assistance.

For example, as illustrated in FIG. 2, the hand portion 200 can include a hand movement assistance component 202 that provides active movement assistance to the fingers via an actuator 204 (e.g., an electric motor, or pneumatic or hydraulic actuator). Other components, such as batteries and the like are not shown for ease of illustration and discussion. The hand portion can also include a passive component 206 that supports the thumb in a semi-rigid manner and enables the thumb of the paretic arm to resist grasp forces during grasp. In order for the movement assistance component 202 to reside on the posterior aspect of the digits, the design should employ a remote center mechanism, such as the remote center linkage 208 operatively coupling rigid digits 209 to the rest of hand portion 200, as shown in FIG. 2. Optionally, the rigid digits 209 can include digit securing elements 210 to facilitate manipulation of the digits. Finally, in order to cause repositioning of the hand of the paretic arm (e.g., open or close the hand), the hand portion 200 can include a button, switch, or control 212 for the hand 200. In some configurations, the hand control 212 can be a toggle switch which can toggle the hand 200 between an open and closed configuration or between any other two or more configurations. Alternatively, hand control 212 can be a lever or rotary switch to allow the hand 200 to alternate between two or more postures. In still other configurations, multiple controls can be provided, where the activated combination of controls can determine the configuration of hand 200 required by user.

In the actuator-assisted embodiment, a powered actuator, such as an electric motor, can be used to assist with the opening or closing of the hand. In the actuated hand portion embodiment, the hand can be toggled between the open and closed configurations with a button or switch located on the hand portion. The button or switch that toggles between the open and closed configurations of the paretic hand can be situated on the thumb. In one embodiment, the thumb portion of the hand orthotic device can be passive, such that the thumb is essentially maintained in a neutral posture, such that only the finger digits are actuated and configured to open or close.

In some cases, the closing of hand 200 can be commanded when a deflection of the digits in the opening direction is detected, for example by a strain sensor or compliant motion sensor associated with the digits. Alternatively, a contact sensor or button on the anterior aspect of the digits could be employed. Similarly, opening of hand 200 can be commanded when a deflection of the digits in the closing direction is detected, such as by a strain sensor or compliant motion sensor, or by a contact sensor or button on the posterior aspect of the digits, or when the button 212 is used to release the grasp. For example, the hand can open or close based on detection of a change in position or force on the digits, such as would be imposed by the non-paretic arm. In one embodiment, if the hand is in the open configuration a movement or force is detected further opening the hand, the hand will move to the closed configuration. In the closed configuration, if movement or force further closing the hand is detected, the hand will move to the open configuration. With this approach, the hand will close around an object when an object is pushed into the hand (such as by the non-paretic arm), deflecting the digits accordingly. Conversely, an object can be released by pushing against posterior aspect of the digits while grasping an object, thus causing the hand to open. In this manner, disturbances that tend to open the hand while grasping an object will not cause accidental release of the object. In another embodiment, the hand open and close is conveyed by a combination of detecting movement or force, and using a button. For example, the hand closing can be initiated by detection of digit opening, while hand opening can be initiated by pressing release control 212 on the hand portion 200.

In some configurations, the configuration of hand portion 200 can vary based on the number and types of postures required for the hand of the paretic arm. In a configuration where the hand is alternated between open and closed positions, a single actuator 204 can be provided, as shown in FIG. 2, that operates the joints of the hand 208 so that the hand and all digits act in concert. In other configurations, multiple actuators can be provided for different parts of the hand. Thus, the hand portion 200 can be utilized to configure the hand in a variety of postures, including controlling each of the digits of the hand separately.

Figure 3:
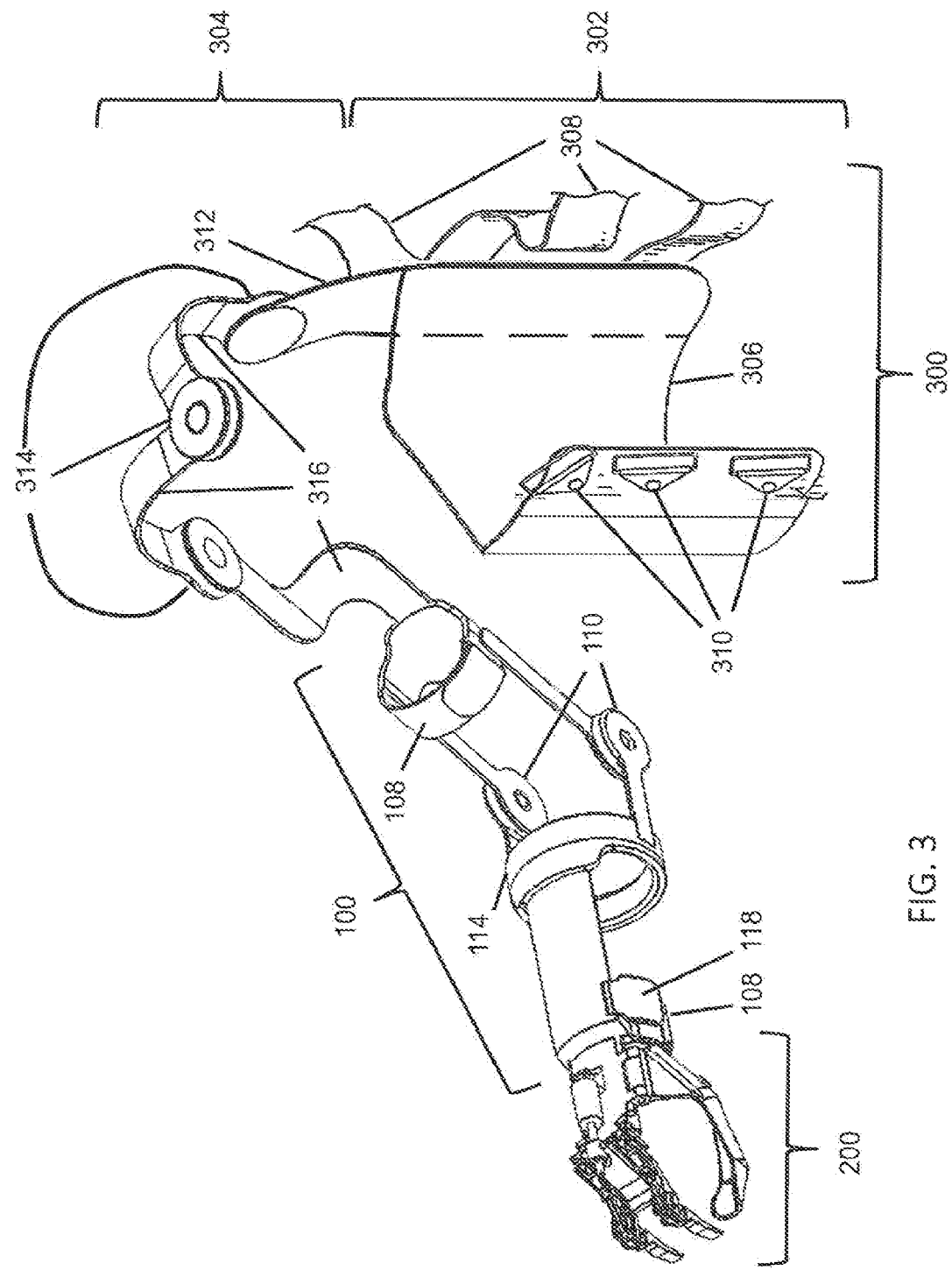
FIG. 3 shows the arrangement of FIG. 2 mated to a shoulder control portion.

As noted above, control of the shoulder joints may not be necessary. However, in other cases, such control may be necessary due to loss of muscle tone, the task the user wishes to perform, or level of impairment. Thus, an orthotic device in accordance with the various embodiments can also include features for controlling a shoulder joint. One exemplary configuration for providing such control is illustrated with respect to FIG. 3. FIG. 3 shows an exemplary configuration for adapting orthotic device 100 to provide manipulation of a shoulder joint. In particular, FIG. 3 shows that orthotic device 100 can be mated with a shoulder control portion 300 including a base section 302 and a shoulder orthosis 304

The base section 302 is configured for attachment to a trunk of a user. As shown in FIG. 3, the base section 302 thus includes a cuff 306 that engages with the trunk of a user. To hold the cuff 306 in place, straps 308 are provided that extend from one side of cuff 306 to wrap over an opposite shoulder of the user and the trunk of the user and engage with retaining elements 310 on another side of cuff 306 to hold cuff 306 in place. The cuff 306 can include rigid or resilient portions to support mounting of elements thereon (e.g., shoulder orthosis 304, as described below) and interior padded portions (not shown) to provide comfort for the user.

The shoulder orthosis 304 can include a support member 312 attached to the cuff 306. The form of attachment is selected to support the weight of the shoulder orthosis 304, orthotic device 100, and (if present) hand portion 200. In general, the support member 312 can be slidably attached or otherwise be repositionable in order to allow adjustment of the position of shoulder control portion 300 and orthotic device 100 to accommodate anatomical differences between different users.

As shown in FIG. 3, at a distal end of the support member 312 a one or more shoulder joints 314 can be provided to allow motion of the paretic arm. As shown in FIG. 3, the shoulder orthosis 304 includes three joints corresponding to the three degrees of freedom in an intact shoulder (internal/ external rotation, flexion/extension, and abduction/adduction). The joints 314 can be mechanically coupled to each other, to support member 312, and to orthotic device by structural portions 320 to attach orthotic device 100 thereto. In the various embodiments, the structural portions 320 can be configured to be adjustable or otherwise be repositionable in order to allow repositioning of the joints 314 with respect to the orthotic device 100 or the structural member 312 to accommodate anatomical differences between for different users.

In some embodiments, the shoulder rotation joints 314 can be normally locked, similar to elbow joint 110 and wrist rotation joint 114. Thus, joints 314 can also include clutch or brake mechanisms, as previously described with respect to FIG. 1. Further, release control 118 can also be configured to operate with joints 314 in shoulder orthosis 304. That is, upon grasping and squeezing the portion of the securing element 108 including the release control 118, near the anatomical wrist joint of the paretic limb, the shoulder orthosis 304 is also configured so that the shoulder joints 314, the elbow joint 110 and the wrist joint 104 are contemporaneously unlocked. Similar to joints 110 and 114, the release control 118 can be operationally coupled to joints 314 via mechanical or electrical means. While unlocked, a user can then reposition the paretic arm, with respect to their shoulder joint, using their non-paretic arm. Once the release control 118 is released by user, the clutch mechanisms in joints 314 are reactivated and the paretic arm is locked into the new pose.

In some configurations, the release control 118 can be limited with respect to the joints it operates (i.e., the clutch/brake mechanisms it releases). For example, in some configurations, the release control 118 can be limited to operating the elbow joint 110 and the wrist rotation joint 114 and a separate release control (not shown) can be provided for shoulder joints 314. This separate control can be located in the vicinity of release control 118 or elsewhere. For example, the separate control (not shown) can be located with securing element 108 in the upper arm portion 104 of orthotic device 100, to allow the user to grasp and reposition in a similar fashion as with release control 118.

Although FIGS. 1-3 show specific configurations for hand portion 200, orthotic device 100, and shoulder control portion 300, the present technology is not limited in this regard. In particular, the number and types of components shown for each of these in FIGS. 1-3 is solely for purposes of illustration. In other embodiments, the number and types of components can vary.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. An orthotic device, comprising:
an upper arm section configured to receive an upper portion of an arm of a subject;
a forearm section configured to receive a forearm portion of the arm; and
at least one elbow joint rotatably coupling the upper arm section and the forearm section, and
wherein the forearm section comprises a release control situated at a distal end of the forearm section and operatively coupled to the at least one elbow joint,
wherein the release control is configured to transition the at least one elbow joint from a restricted motion state to a free motion state when the release control is activated,
wherein the release control is at a location on the distal end of the forearm section that coincides with a location of a wrist of the subject,
wherein the release control comprises at least one of a lever or button that is activated by applying a force to at least a portion of the forearm section associated with a location of the release control,
wherein the release control is configured to maintain the at least one elbow joint in the free motion state only while the force is applied,
wherein the release control is configured to toggle the at least one elbow joint between the restricted motion state and the free motion state when activated.

2. The device of claim 1, wherein the at least one elbow joint comprises a mechanically-actuated clutch mechanism operatively coupled to the release control with a cable, wherein the release control is configured to pull the cable when activated, and wherein the pulling of the cable releases the mechanically-actuated clutch mechanism to provide free motion of the at least one elbow joint.

3. The device of claim 2, wherein the mechanically-actuated clutch mechanism is of a friction clutch type, a dog clutch type, a wrapped spring clutch type, or a belt clutch type.

4. The device of claim 1, wherein the at least one elbow joint comprises an electrically-actuated clutch mechanism communicatively coupled to the release control, and wherein the activation of the release control is configured to operate the electrically-actuated clutch mechanism to provide free motion of the at least one elbow joint.

5. The device of claim 4, wherein the electrically-actuated clutch mechanism comprises at least one of an electromagnetic type, an electrorheological type, a magnetorheological type, or a magnetic particle type.

6. The device of claim 1, further comprising a passively repositionable wrist joint.

7. The device of claim 1, further comprising a hand portion with a plurality of linkages configured to provide assistance to at least a portion of a hand of the arm.

8. The device of claim 7, further comprising a plurality of elastic elements to assist with at least opening or closing of digits of the portion of the hand.

9. The device of claim 7 further comprising at least one powered actuator to actively assist with at least the opening or closing of the portion of the hand.

10. The device of claim 7, wherein the hand portion provides passive resistance to digit motion.

11. The device of claim 7, wherein the hand portion comprises a thumb portion configured for providing passive resistance to thumb motion.

12. The device of claim 7, wherein the hand portion further comprises a hand control configured to alternate the hand portion between two or more postures when activated.

13. The device of claim 7, wherein hand portion is configured to toggle the hand portion between an open configuration and a closed configuration when a transient motion or a change in force in the hand portion is detected.

14. The device of claim 13, wherein the hand portion is toggled from the open configuration to the closed configuration when the transient movement or the change in force is detected in the direction of opening the hand.

15. The device of claim 13, wherein the hand portion is toggled from the closed configuration to the open configuration when the transient movement or the change in force is detected in the direction of closing the hand.

* * * * *